(12) United States Patent
Clerc et al.

(10) Patent No.: US 11,298,442 B2
(45) Date of Patent: Apr. 12, 2022

(54) DISSOLVABLE OR DEGRADABLE ADHESIVE POLYMER TO PREVENT STENT MIGRATION

(71) Applicant: Boston Scientific Scimed, Inc., Maple Grove, MN (US)

(72) Inventors: Claude O. Clerc, Marlborough, MA (US); Gerald Fredrickson, Westford, MA (US); Mark Boden, Harrisville, RI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/012,522

(22) Filed: Aug. 28, 2013

(65) Prior Publication Data

US 2015/0045876 A1   Feb. 12, 2015

Related U.S. Application Data (60) Provisional application No. 61/863,584, filed on Aug. 8, 2013.

(51) Int. Cl.
| | |
|---|---|
| A61L 27/58 | (2006.01) |
| A61F 2/82 | (2013.01) |
| A61L 31/14 | (2006.01) |
| A61L 31/10 | (2006.01) |

(52) U.S. Cl.
CPC ............... *A61L 27/58* (2013.01); *A61F 2/82* (2013.01); *A61L 31/10* (2013.01); *A61L 31/148* (2013.01)

(58) Field of Classification Search
None
See application file for complete search history.

(56) References Cited

U.S. PATENT DOCUMENTS

| | | | |
|---|---|---|---|
| 5,405,366 A | 4/1995 | Fox et al. | |
| 5,618,551 A | 4/1997 | Tardy et al. | |
| 5,693,034 A | 12/1997 | Buscemi et al. | |
| 6,013,854 A * | 1/2000 | Moriuchi | A61F 2/91 606/194 |
| 6,176,849 B1 | 1/2001 | Yang et al. | |

(Continued)

FOREIGN PATENT DOCUMENTS

| | | |
|---|---|---|
| JP | 2002534165 | 10/2002 |
| JP | 2004261567 A | 9/2004 |

(Continued)

OTHER PUBLICATIONS

U.S. Appl. No. 61/394,104, filed Oct. 18, 2010, inventor Rajesh Radhakrishnan et al.

(Continued)

*Primary Examiner* — Leslie Lopez
(74) *Attorney, Agent, or Firm* — Seager, Tufte & Wickhem, LLP (57) ABSTRACT

A stent having an inner surface and an outer surface, at least a portion of the outer surface of the stent comprising a dissolvable adhesive polymer or a degradable adhesive polymer disposed on at least a portion of the outer surface of the stent, the adhesive is activated by exposure to an aqueous environment, the dissolvable adhesive polymer dissolves over time in an aqueous environment, the dissolvable adhesive polymer or the degradable adhesive polymer has a surface tack of about 2 psi to about 14 psi.

18 Claims, 11 Drawing Sheets

(56) References Cited

U.S. PATENT DOCUMENTS

| | | | |
|---|---|---|---|
| 6,251,136 B1 | 6/2001 | Guruwaiya et al. | |
| 6,379,379 B1 | 4/2002 | Wang | |
| 6,447,835 B1 | 9/2002 | Wang et al. | |
| 6,589,215 B2 | 7/2003 | Yang et al. | |
| 6,610,035 B2 | 8/2003 | Yang et al. | |
| 6,624,245 B2 | 9/2003 | Wallace et al. | |
| 6,656,214 B1* | 12/2003 | Fogarty | A61F 2/07 623/1.13 |
| 6,805,898 B1 | 10/2004 | Wu et al. | |
| 7,223,286 B2* | 5/2007 | Wright | A61F 2/91 623/1.42 |
| 7,767,220 B2 | 8/2010 | Ranade et al. | |
| 8,114,147 B2 | 2/2012 | Wood et al. | |
| 8,147,866 B2 | 4/2012 | Finn et al. | |
| 8,221,783 B2 | 7/2012 | Helmus et al. | |
| 8,247,598 B2 | 8/2012 | Fang et al. | |
| 8,263,704 B2 | 9/2012 | Stopek et al. | |
| 2003/0032734 A1 | 2/2003 | Roby | |
| 2004/0215169 A1 | 10/2004 | Li | |
| 2005/0110214 A1* | 5/2005 | Shank et al. | 273/274 |
| 2006/0036311 A1 | 2/2006 | Nakayama et al. | |
| 2006/0069425 A1 | 3/2006 | Hillis et al. | |
| 2006/0167540 A1 | 7/2006 | Masters et al. | |
| 2006/0276887 A1 | 12/2006 | Brady et al. | |
| 2007/0255388 A1* | 11/2007 | Rudakov | A61F 2/07 623/1.11 |
| 2008/0009934 A1 | 1/2008 | Schneider et al. | |
| 2008/0071350 A1 | 3/2008 | Stinson | |
| 2008/0071358 A1 | 3/2008 | Weber et al. | |
| 2009/0018648 A1 | 1/2009 | Wittchow | |
| 2009/0062927 A1 | 3/2009 | Marten et al. | |
| 2009/0082840 A1 | 3/2009 | Rusk et al. | |
| 2009/0098176 A1* | 4/2009 | Helmus et al. | 424/422 |
| 2009/0104244 A1* | 4/2009 | Flanagan | A61L 31/10 424/423 |
| 2009/0138070 A1* | 5/2009 | Holzer | A61F 2/07 623/1.15 |
| 2009/0187240 A1* | 7/2009 | Clerc et al. | 623/1.17 |
| 2009/0312834 A1 | 12/2009 | Wood et al. | |
| 2010/0069838 A1 | 3/2010 | Weber et al. | |
| 2010/0087783 A1 | 4/2010 | Weber et al. | |
| 2010/0241214 A1* | 9/2010 | Holzer et al. | 623/1.15 |
| 2010/0316712 A1 | 12/2010 | Nangia et al. | |
| 2011/0071498 A1 | 3/2011 | Hakimimehr et al. | |
| 2011/0213410 A1* | 9/2011 | Ginn | A61F 2/954 606/213 |
| 2011/0262520 A1 | 10/2011 | Dormady et al. | |
| 2012/0035715 A1 | 2/2012 | Robida et al. | |
| 2012/0095396 A1 | 4/2012 | Radhakrishnan et al. | |
| 2012/0123521 A1 | 5/2012 | Headley, Jr. et al. | |
| 2012/0128793 A1 | 5/2012 | Miller et al. | |
| 2013/0231753 A1* | 9/2013 | Liddy | A61L 31/10 623/23.7 |

FOREIGN PATENT DOCUMENTS

| | | |
|---|---|---|
| JP | 2013027714 A | 2/2013 |
| WO | 2000/040278 | 7/2000 |
| WO | 0040278 | 7/2000 |
| WO | 2006/038866 | 4/2006 |

OTHER PUBLICATIONS

Tao et al., "Bioadhesive poly(methyl methacrylate) microdevices for controlled drug delivery", Journal of Controlled Release, 88, (2003), 215-228.

http://en.wikipedia.org/wiki/Bioadhesive#Mucoadhesion.

Johanson et al., "Incidence and risk factors for biliary and pancreatic stent migration," Gastrointestinal Endoscopy, May-Jun. 1992; 38(3): 341-6.

Lim et al., "The adhesive properties of coacervated recombinant hybrid mussel adhesive proteins", Biomaterials, 31, (2010), 3715-3722.

Park et al., "Mechanisms of Mucoadhesion of Poly(acrylic Acid) Hydrogels," Pharmaceutical research, 1987, vol. 4, No. 6, 457-464.

Dowding et al., "Preparation and Swelling Properties of Poly(NIPAM) "Minigel" Particles Prepared by Inverse Suspension Polymerization", Journal of Colloid and Interface Science 221, 268-272 (2000), available online at http://www.idealibrary.com.

Sekiyama et al., "Novel Sutureless Transplantation of Bioadhesive-Coated, Freeze-Dried Amniotic Membrane for Ocular Surface Reconstruction", Investigative Ophthalmology & Visual Science, Apr. 2007, vol. 48, No. 4, 1528-1534.

Khutoryanskiy, "Advances in Mucoadhesion and Mucoadhesive Polymers," Macromolecular Bioscience, 2011,11, pp. 748-764; Jim 14; 1J(6):748-64. doi: 10.1002/mabi.201000388.Epub Dec. 27, 2010.

* cited by examiner

DISSOLVABLE OR DEGRADABLE ADHESIVE POLYMER TO PREVENT STENT MIGRATION

CROSS-REFERENCE TO RELATED APPLICATIONS

This application claims priority to U.S. Patent Provisional Application No. 61/863,584, filed Aug. 8, 2013, the entire contents of which are hereby incorporated herein by reference.

BACKGROUND OF THE INVENTION

The present invention relates generally to covered medical devices, in particular, to covered stents and to methods of using a tacky polymeric material in a patient's body lumen to prevent stent migration from a treatment site.

Stents, grafts, stent-grafts, vena cava filters and similar implantable medical devices, collectively referred to hereinafter as stents, are radially expandable or self-expanding endoprostheses which are intravascular or endoscopic implants capable of being implanted transluminally either percutaneously, uroscopically or endoscopically. Stents may be implanted in a variety of body lumens or vessels such as within the vascular system, urinary tracts, bile ducts, gastrointestinal tract including the esophagus, the biliary and the colon, airways, etc. Stents may be used to reinforce body vessels and to prevent restenosis following angioplasty in the vascular system. They may be self-expanding, mechanically expandable or hybrid expandable. In general, self-expanding stents are mounted on a delivery device consisting of two tubes. The stent is delivered by sliding the outer tube to release the stent.

Stents are typically tubular members that are radially expandable from a reduced diameter configuration for delivery through a patient's body lumen to an expanded configuration once deployed at the treatment site.

Stents may be constructed from a variety of materials such as stainless steel, Elgiloy®, nickel, titanium, nitinol, shape memory polymers, other polymeric materials, etc. For metallic stents, a stent may be typically formed from a tubular member, either extruded or formed from a sheet, in which a pattern is subsequently formed by etching or cutting material from the tubular member. Metallic stents may also be formed formed by weaving, knitting or braiding fibers or filaments.

Polymeric stents formed from a variety of thermoplastic polymer materials may be formed by weaving, knitting or braiding fibers or filaments. They can also be formed from extruded sheets, cut into desired shapes and bonded or otherwise formed into tubes. The shapes can be formed by stamping, laser cutting, or compression molded, for example. The tubes can be heated welded, ultrasonically welded, glued with adhesives, solvent bonded, or joined by any other suitable means.

Polymeric stents can also be formed by solvent or thermally extruded "writing" methods. For example, thin beads of polymer is a suitable solvent can be deposited in the desired shape around a mandrel, in which case the struts are solvent bonded. 3D printers, or piston extruders can be used to melt and deposit liquid polymer on a mandrel.

Stents may further be provided with a cover, such as a silicone cover to prevent tissue ingrowth. Stents of this type are described in commonly assigned US Patent Publication Nos. 2006/0276887 and 2008/0009934, each of which is incorporated by reference herein in its entirety.

The stent need not be covered whatsoever, may be partially covered or may be fully covered.

Other suitable covering materials can be employed as well. Examples of other suitable covering materials include, but are not limited to, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene, dicarboxylate derivatives, such as polyethylene naphthalate, polybutylene naphthalate, polytrimethylene naphthalate and trimethylenediol naphthalate, polyurethane, polyurea, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. See, for example, commonly assigned U.S. Pat. No. 8,114,147, the entire content of which is incorporated by reference herein.

Desirable stent properties include sufficient flexibility to be able to conform to the tortuous body lumen during delivery yet sufficient radial force to open the body lumen at the treatment site.

In some stents, the compressible and flexible properties that assist in stent delivery may also result in a stent that has a tendency to migrate from its originally deployed position. The stent covering may contribute to migration as well. Stent migration affects many endoscopic stents including esophageal, colorectal, airway, pancreatic and biliary stents. Risk factors associated with stent migration are discussed in *Incidence and risk factors for biliary and pancreatic stent migration, Johanson J F, Schmah. M J, Geenen J E. Gastrointest Endosc.* 1992 May-June; 38(3): 341-6.

Esophageal stents are particularly susceptible to stent migration due to the structure of the esophagus and conditions therein such as peristalsis.

Moreover, fully covered stents prevent tissue ingrowth and are easier to remove than bare or partially covered stents. However, these stents are even more prone to migration. The incidence of migration for a fully covered stent in pulmonary and esophageal indication is about 10-50% depending on the indication and the stent. Migration can occur immediately after implantation to several months after implantation.

For temporary stents, typical removal times are 6-8 weeks after implantation. Suitably, the adhesive dissolves between about 4 and about 6 weeks after implantation.

It is thus desirable to provide a stent configuration that resists migration following deployment.

One way to reduce the risk of stent migration has been to expose bare metal portions of the stent to esophageal tissue. The open, braided structure of the stent provides a scaffold that promotes tissue ingrowth into the stent. This tissue ingrowth anchors the stent in place and greatly reduces the risk of migration. However, tissue ingrowth may lead to reocclusion of the esophagus. In addition, esophageal stents anchored by tissue ingrowth cannot be moved or removed without an invasive procedure. To reduce tissue ingrowth, stents have been covered with a polymer covering to create a physical barrier between the lumen and the esophageal wall. However, traditional polymer covered esophageal stents have higher rates of migration than their bare metal counterparts.

Another way to reduce the risk of stent migration has been to use a flared stent in the esophagus. However, stents are susceptible to migration even with flares.

Another method of reducing stent migration has been to provide surface features such as bumps or protrusions or other surface features such as disclosed in US Patent Publication Nos. 2006/0069425 and 2009/0062927, and in commonly assigned 2012/0035715, each of which is incorporated by reference herein in its entirety.

Commonly assigned US Patent Publication No. 20090098176, the entire content of which is incorporated by reference herein, discloses medical devices with triggerable bioadhesives.

Many techniques have been developed to prevent stent migration including adding barbs and flares to the stent itself or using clips or sutures to attach the stent to the vessel wall.

There remains a need in the art for an improved stent that is resistant to migration.

SUMMARY OF THE INVENTION

In one embodiment, the present invention relates to a stent having an inner surface and an outer surface, at least a portion of the outer surface of the stent comprising a dissolvable adhesive polymer or a degradable adhesive polymer disposed on at least a portion of the outer surface of the stent, the adhesive is activated by exposure to an aqueous environment, the dissolvable adhesive polymer dissolves over time in an aqueous environment, the dissolvable adhesive polymer or the degradable adhesive polymer has a surface tack of about 2 psi to about 14 psi.

In another embodiment, the present invention relates to a stent, the stent having an inner surface and an outer surface, at least a portion of the outer surface of the stent comprising a two-part dissolvable adhesive polymer or a two-part degradable adhesive polymer wherein the first part is disposed on the outer surface of the stent and the second part is disposed in a body lumen to be treated, the dissolvable adhesive polymer or the degradable adhesive polymer is activated upon contact of the first part and the second part.

In another embodiment, the present invention relates to a method of delivering a stent to a body lumen, the method comprising depositing a dissolvable adhesive polymer or a degradable adhesive polymer at a treatment site in a body lumen, delivering the stent to the treatment site and deploying the stent at the treatment site, wherein the dissolvable adhesive polymer or the degradable adhesive polymer hinders migration of the stent from the treatment site.

In another embodiment, the present invention relates to a method of delivering a stent to a body lumen, the method comprising depositing a dissolvable or degradable adhesive polymer on the outer surface of the stent, delivering the stent to the treatment site and deploying the stent at the treatment site, wherein the dissolvable adhesive polymer or the degradable adhesive polymer hinders migration of the stent from the treatment site.

In another embodiment, the present invention relates to a method of delivering a stent to a body lumen, the method comprising depositing a dissolvable or degradable adhesive polymer on the outer surface of the stent, depositing a dissolvable adhesive polymer or a degradable adhesive polymer at a treatment site in a body lumen, delivering the stent to the treatment site and deploying the stent at the treatment site, wherein the dissolvable adhesive polymer or the degradable adhesive polymer hinders migration of the stent from the treatment site.

These and other aspects, embodiments and advantages of the present disclosure will become immediately apparent to those of ordinary skill in the art upon review of the Detailed Description and Claims to follow.

DETAILED DESCRIPTION OF THE INVENTION

While this invention may be embodied in many forms, there are described in detail herein, specific embodiments of the present disclosure. This description is an exemplification of the principles of the present disclosure and is not intended to limit the disclosure to the particular embodiments illustrated herein.

Figure 1:
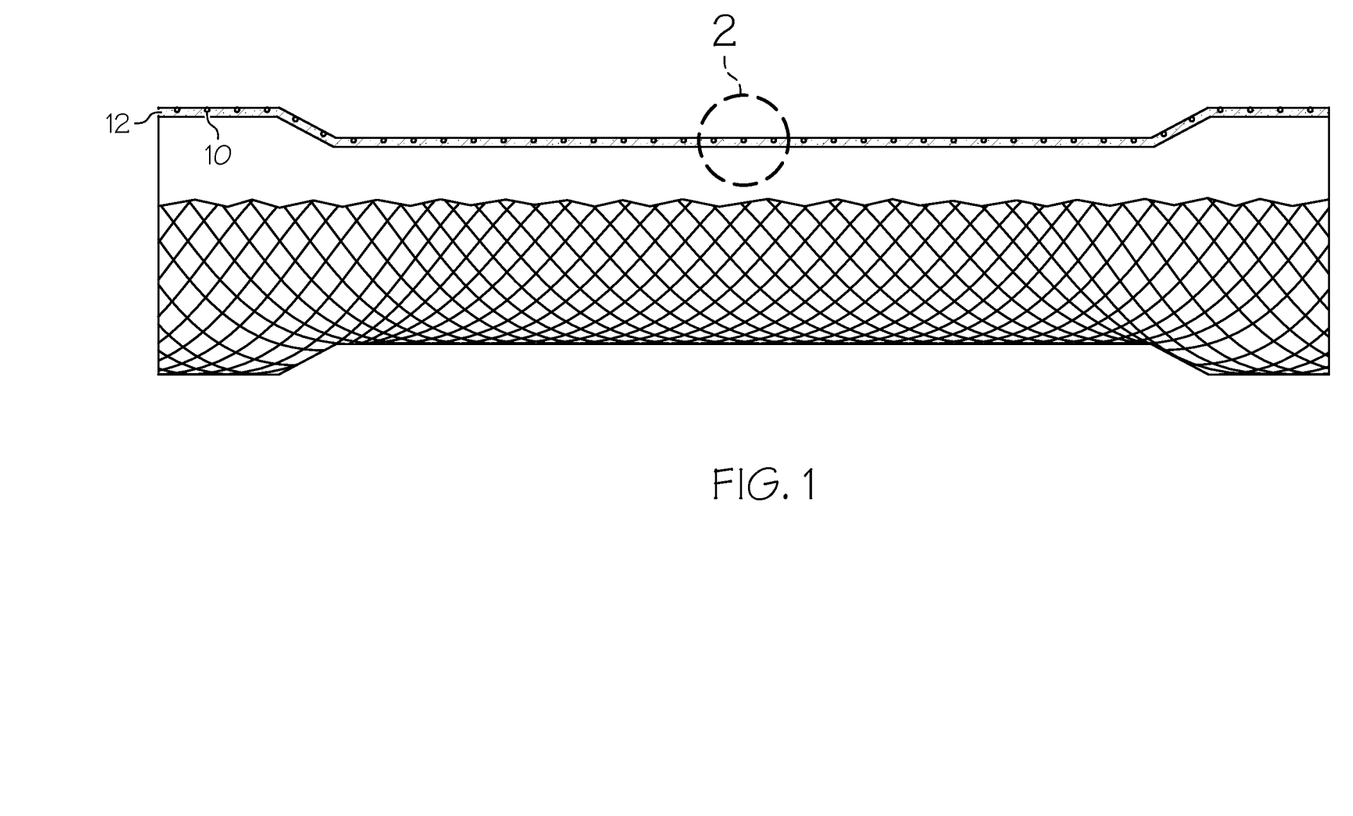
FIG. 1 is a side view of an embodiment of a stent according to the invention.
Figure 2:
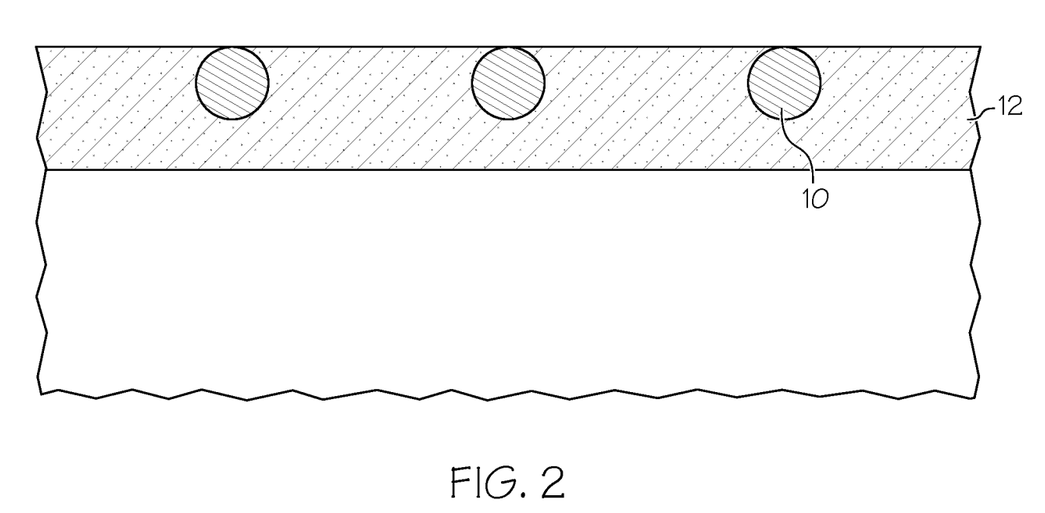
FIG. 2 is a cross-sectional view taken at 2 in FIG. 1 illustrating the tacky polymeric coating on the stent according to the invention.

Turning now to the drawings, FIG. 1 is a side view of one embodiment of a stent on which the coatings according to the invention be employed. In this embodiment, stent 10 is a self-expanding stent formed of a shape memory metal such as nitinol having a silicone covering. The stent has a braided wire construction. In this embodiment, stent 10 is shown having a silicone covering 12. Stent 10 is disposed on silicone covering 12 and is partially embedded therein. FIG. 2 is a partial cross-sectional view of the stent taken at section 2 in FIG. 1. Stents of this type are described in commonly assigned US Patent Publication Nos. 2006/0276887 and 2008/0009934, each of which is incorporated by reference herein in its entirety.

While in the embodiment shown in FIGS. 1 and 2, the stent is formed from nitinol, stents may be constructed of any suitable stent material including, but not limited to stainless steel, Elgiloy, nickel, titanium, nitinol, shape memory polymers, other polymeric materials, etc.

Thermoplastic polymer materials which may be employed in forming the device include both elastomeric and non-elastomeric materials, examples of which include, but are not limited to, polyolefins such as metallocene catalyzed polyethylenes, polypropylenes, and polybutylenes, polycyclooctenes, and copolymers thereof; vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with cations, for example zinc or sodium ions (commonly known as ionomers); alkyl acrylates and methacrylate polymers and copolymers, polyacetals; chloropolymers such as polyvinylchloride (PVC); fluoropolymers such as polytetrafluoroethylene (PTFE); polyesters such as polyethyleneterephthalate (PET); polyester-ethers; polyamides such as nylon 6 and nylon 6,6; polyamide ethers; polyethers; elastomers such as elastomeric polyurethanes and polyurethane copolymers; polycarbonates; methylmethacrylate N-vinylpyrrolidone copolymers; poloyvinyl alcohol (PVA); poly(ethylene oxide) (PEO); and blends, mixtures and block or random copolymers of any of the foregoing.

Stent 10 may also optionally be formed at least partially, or entirely of a biodegradable or bioabsorbable polymer material. Examples include, but are not limited to, poly (alpha-hydroxy acid) polymers and copolymers, such as polymers and copolymers of glycolide including polyglycolide (PGA), poly(glycolide-co-lactide)(PGLA), and poly (glycolide-co-trimethylene carbonate(PGA/TMC; polymers and copolymers of polylactide (PLA) including poly-L-lactide (PLLA), poly-D-lactide (PDLA), poly-DL-lactide (PDLLA), poly(lactide-co-tetramethylene glycolide), poly (lactide-co-trimethylene carbonate), poly(lactide-co-delta-valerolactone), poly(lactide-co-epsilon-caprolactone), poly (glycine-co-DL-lactide) and poly(lactide-co-ethylene oxide); polydioxanone polymers such as asymmetrically 3,6-substituted poly-1,4-dioxane-2,5-diones; poly(beta-hydroxybutyrate) (PHBA) and copolymers of the same such as poly(beta-hydroxybutyrate-co-beta-hydroxyvalerate); polygluconate; poly(beta-hydroxypropionate) (PHPA); poly (beta-dioxanone)(PDS); poly(valerolactone); poly(caprolactone); polyester amides; polyesters of oxalic acid; polydihydropyranes; poly(alkyl-2-cyanoacrylate); polypeptides; poly(beta-maleic acid) (PMLA); poly(beta-alkanoic acid); tyrosine polycarbonates; tyrosine polyeyesters; polyanhydrides; polyphosphoester; polyurethanes with degradable soft segments such as PLA, PLGA, and so forth; chitin polymers; and blends, mixtures, block, and dendrimers of the polymers. See, for example, commonly assigned US Patent Publication No. 20120123521, the entire content of which is incorporated by reference herein. This patent also illustrates various stent designs which can be employed herein.

Any stent can have a covering and the coverings are thus not limited to nitinol stents. Moreover, the stent need not be covered whatsoever, may be partially covered or may be fully covered.

Other suitable covering materials can be employed as well. Examples of other suitable covering materials include, but are not limited to, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene, dicarboxylate derivatives, such as polyethylene naphthalate, polybutylene naphthalate, polytrimethylene naphthalate and trimethylenediol naphthalate, polyurethane, polyurea, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. See, for example, commonly assigned U.S. Pat. No. 8,114,147, the entire content of which is incorporated by reference herein.

Figure 3:
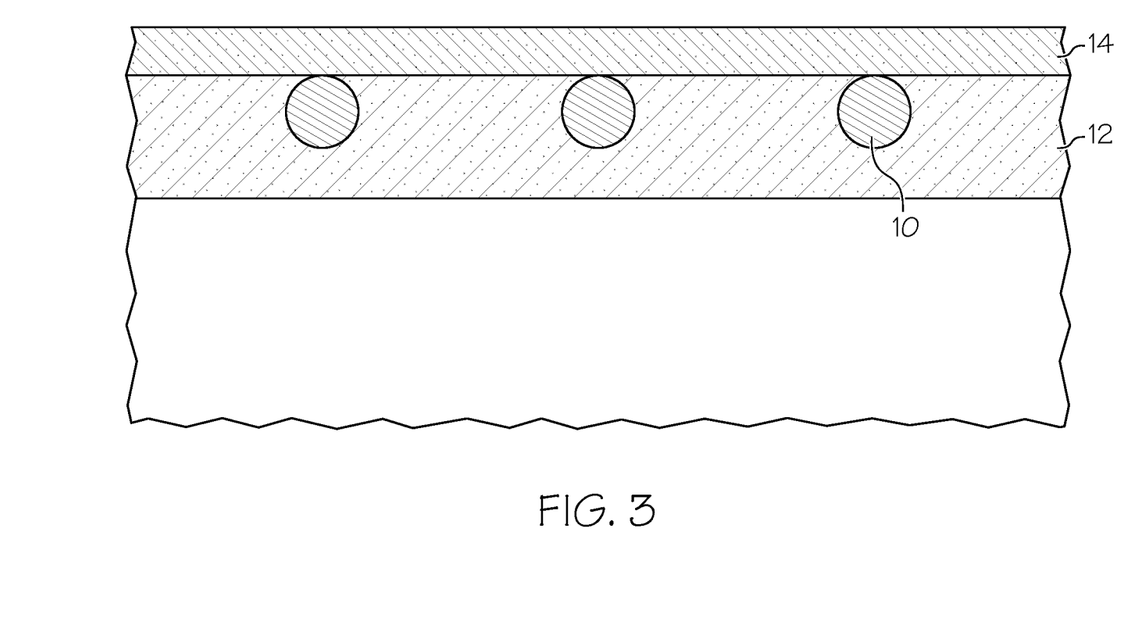
FIG. 3 is a cross-sectional view of an alternative embodiment of a stent similar to that shown in FIG. 1 having the tacky polymeric coating and a hydrophilic coating or biodegradable coating disposed on the tacky polymeric coating.

Stent 10 further includes a dissolvable or degradable adhesive polymer coating 14 as shown in cross-section in FIG. 3. The dissolvable or degradable adhesive polymer temporarily hinders migration of the stent from the treatment site but dissolves in a patient's body over time allowing removal of the stent if desired. Suitably, the adhesive polymer exhibits an adhesion surface tack of about 1 psi to about 15 psi and more suitably about 2 psi to about 14 psi. Exemplary adhesives include, but are not limited to, cellulose and derivatives thereof, carbohydrates, glycoproteins, and mucopolysaccharides.

Examples of degradable adhesive polymers include, but are not limited to, starches, fibrin glues and protein based adhesives.

Suitably, the dissolvable or degradable adhesive polymer is selected so as to dissolve or degrade within the body within about 1 week and up to 90 days. As discussed above, for temporary stents, typical removal times are 6-8 weeks after implantation. Suitably, the adhesive dissolves or degrades between about 4 and about 6 weeks after implantation.

Suitably, the dissolvable or degradable adhesive polymer is a synthetic polymer material. This allows for selection of the desirable dissolution or degradation rate by controlling the molecular weight of the polymer, the types of functional groups on the polymer, the type of chemical bonds present in the polymer backbone, and so forth.

The dissolvable or degradable adhesive may be applied to all of the stent or to a portion or portions of the stent. For example, the adhesive can be disposed about the distal, middle and proximal portions of the stent or any combination thereof.

Suitably, the dissolvable or degradable adhesive is the only coating on the stent.

Figure 5:
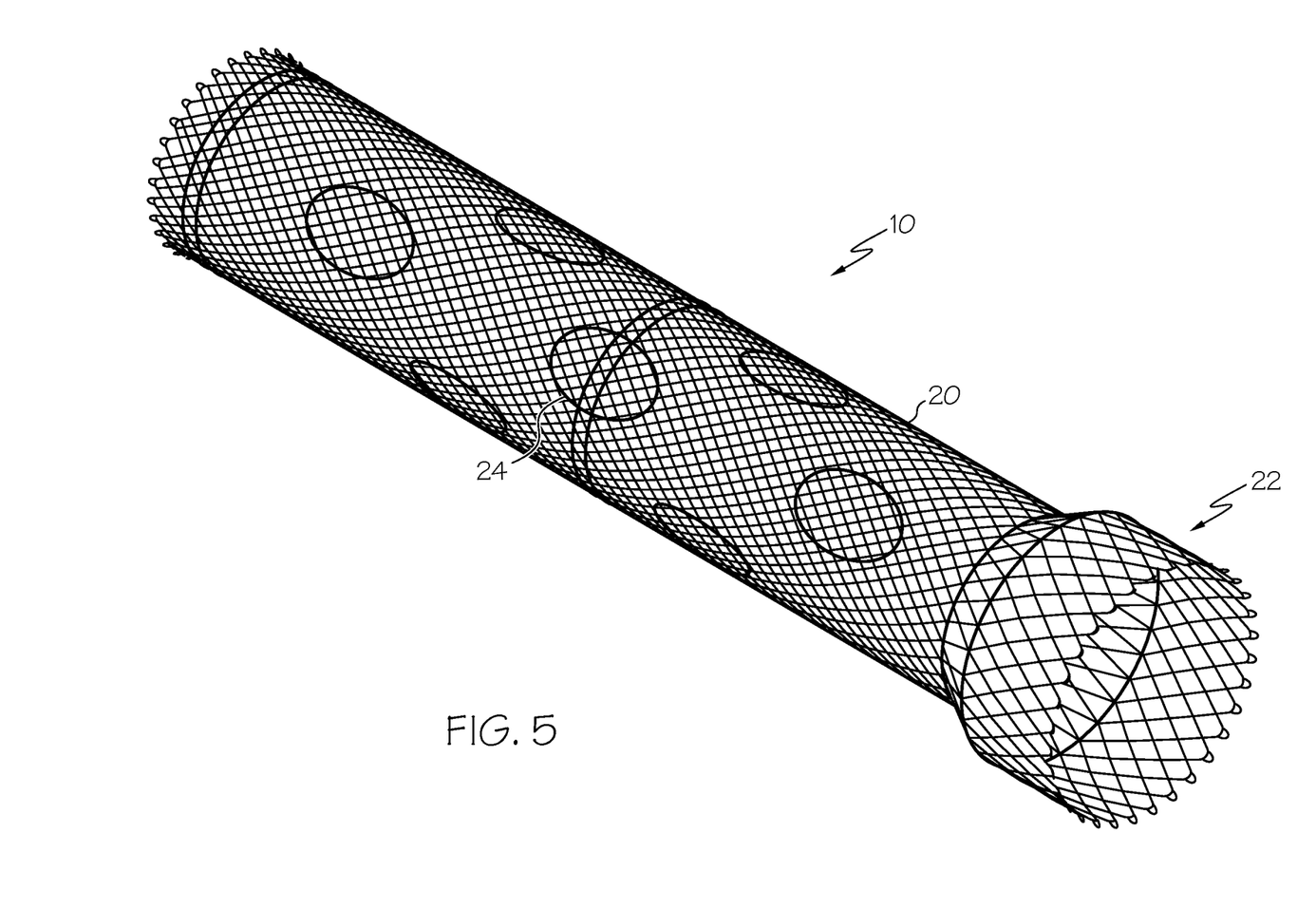
FIG. 5 is a perspective view of an exemplary stent having patches of adhesive disposed thereon.
Figure 6:
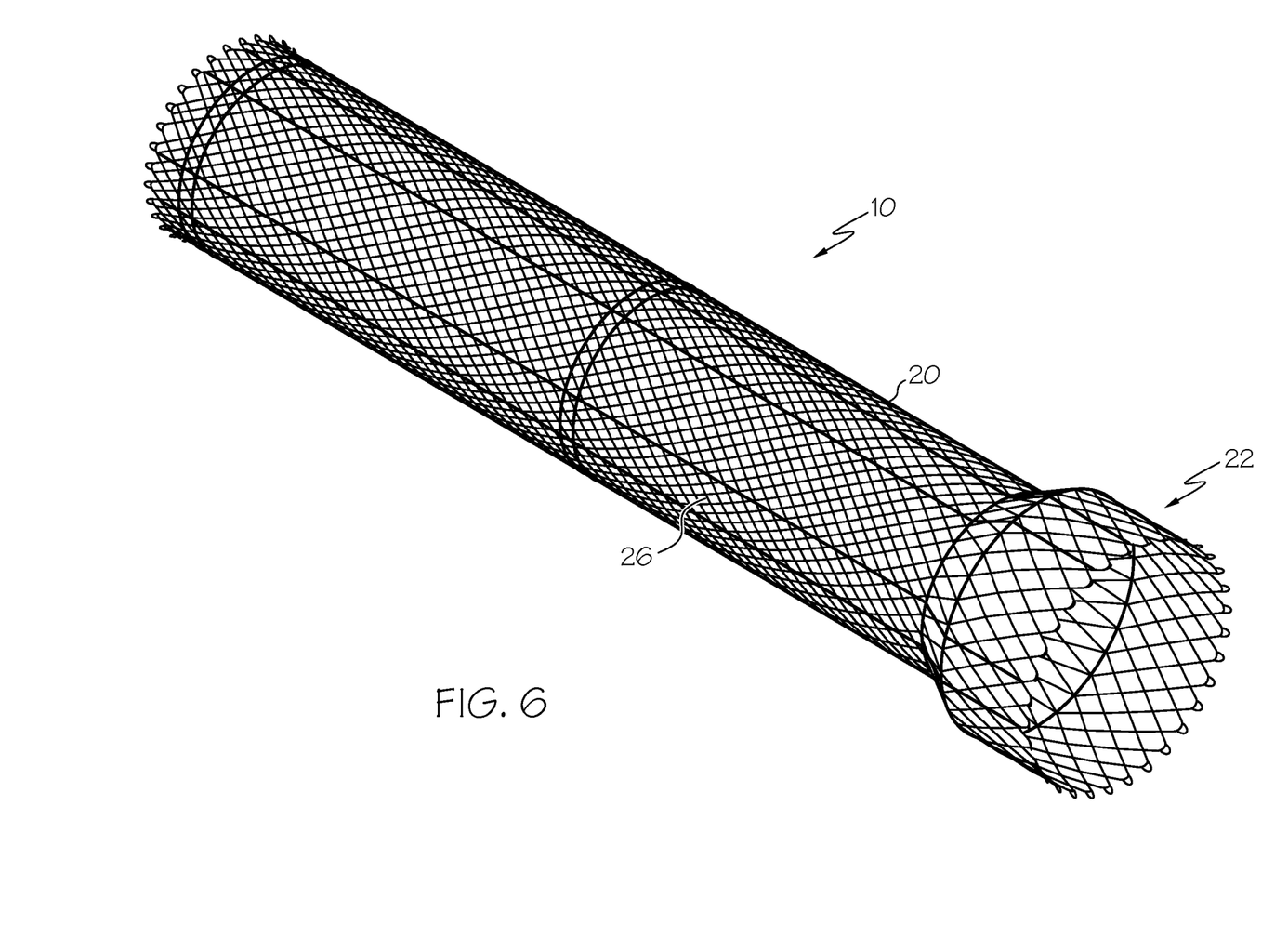
FIG. 6 is a perspective view of an exemplary stent having longitudinal stripes of adhesive disposed thereon.
Figure 7:
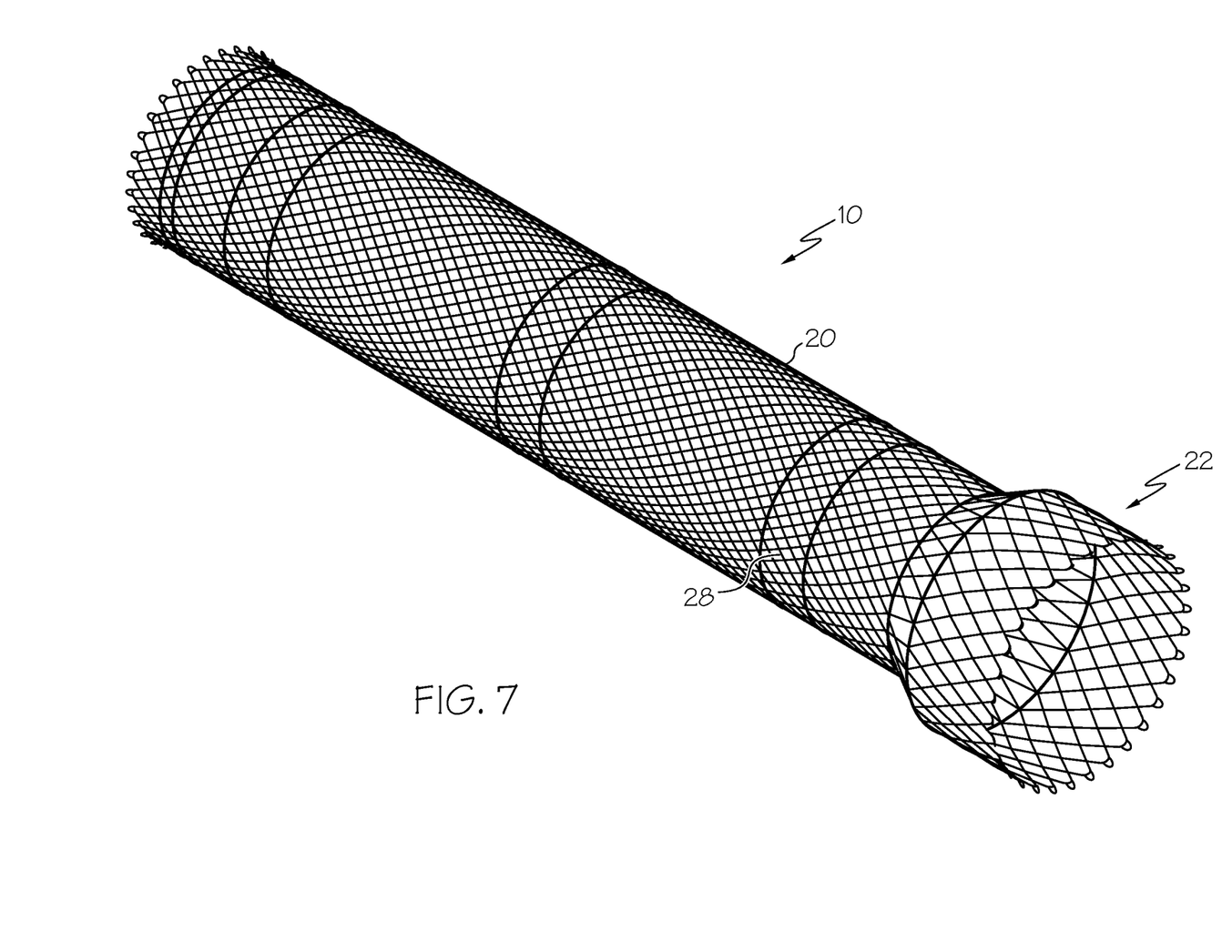
FIG. 7 is a perspective view of an exemplary stent having adhesive in circumferential circles disposed thereon.

FIGS. 5-7 illustrate various patterns in which the adhesive may be either disposed about the stent, or pre-delivered to a body lumen prior to delivery of the stent, or may be applied both to the stent and pre-delivered to a body lumen.

FIG. 5 illustrates an embodiment wherein the dissolvable polymer adhesive is disposed on the stent 10 or delivered to the body lumen in a plurality of patches 24. One or more patches may be employed.

FIG. 6 illustrates an embodiment wherein the dissolvable polymer adhesive is disposed on the stent 10 or pre-delivered to a body lumen in the form of a plurality of longitudinal stripes 26. One or more longitudinal stripes may be employed.

FIG. 7 illustrates an embodiment wherein the dissolvable adhesive polymer is disposed on the stent 10 or pre-delivered to a body lumen in the form of a plurality of circumferentially disposed stripes 28. One or more circumferential stripes may be employed.

In some embodiments, the stent is an endoscopic stent.

In some embodiments, the stent is an esophageal stent, pancreatic stent, duodenal stent, colonic stent, biliary stent or an airway stent.

Figure 4:
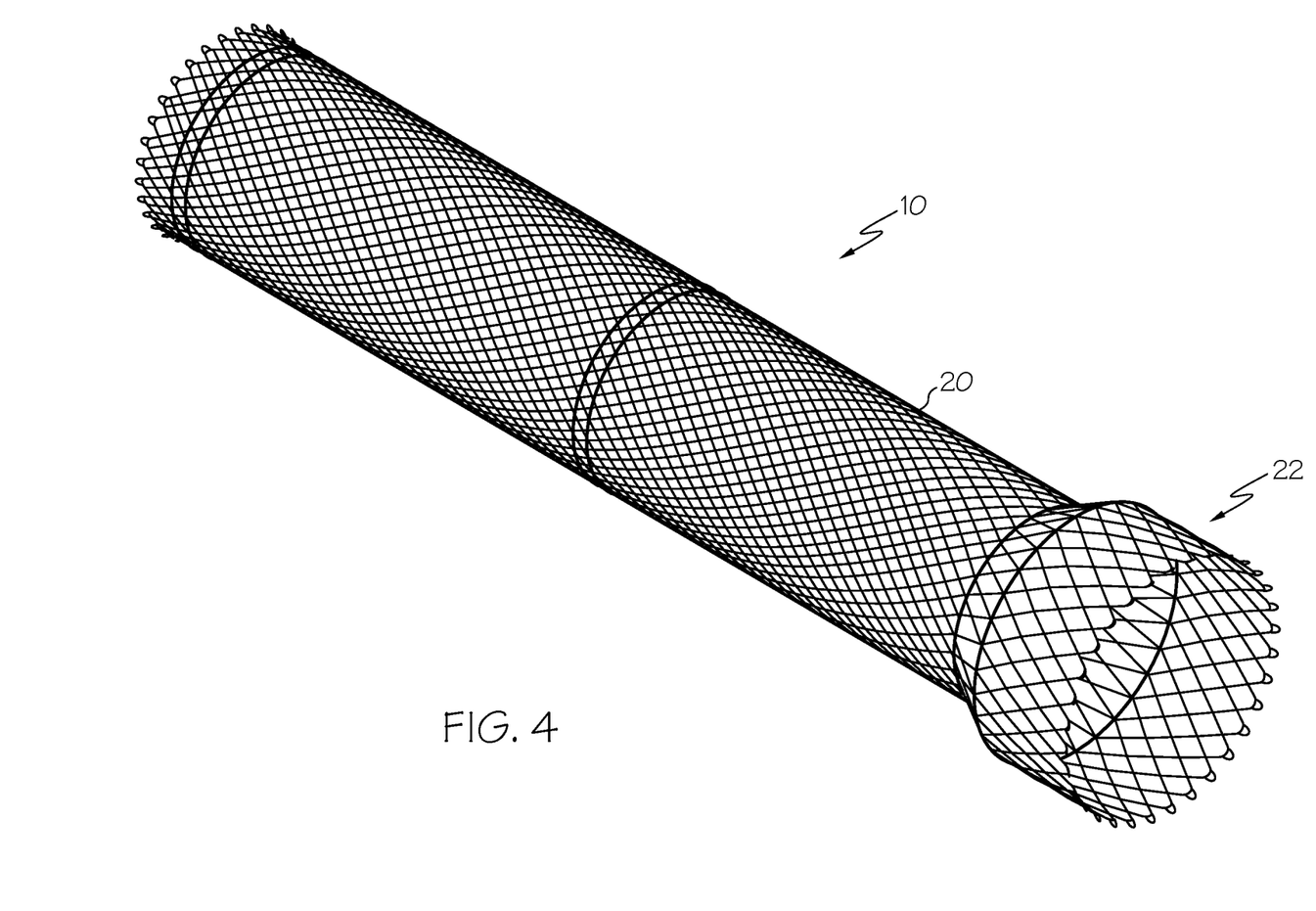
FIG. 4 is a perspective view of an exemplary stent on which the coatings may be employed.

FIG. 4 is a perspective view of an endoscopic stent 10 on which the coatings may be employed. Stent 10 may be coiled or patterned as a braided or woven open network or fibers or filaments as disclosed, for example, in commonly assigned US Patent Publication No. 2012/0128793, the entire content of which is incorporated by reference herein.

In some embodiments, the stent has at least one flared end.

In one embodiment, stent 10 has a braided construction 20 and a flared proximal end 22. In this embodiment, stent 10 is an esophageal stent. Stent 10 may be formed of any suitable stent material including metallic and non-metallic materials as well as shape memory materials. Examples of suitable materials include, but are not limited to, shape memory alloys such as Nitinol®, other metallic materials such as stainless steel, tantalum, titanium, nickel-chrome, or cobalt-chromium alloys such as those sold under the tradename of Elgiloy®.

In one embodiment, the stent is a polymeric self-expanding stent formed from polyethylene terephthalate (PET) filaments having a silicone covering. These types of stents are commercially available from Boston Scientific Inc. located in Natick, Mass. under the tradename of Polyflex®.

Another example of a covered stent is a self-expanding nitinol stent formed of braided or woven wires and having a silicone covering. These types of stents are commercially available from Boston Scientific Inc. located in Natick, Mass. under the tradename of WallFlex®.

Another example of a covered stent is a self-expanding nitinol stent formed of braided or woven wires and having a polyurethane covering. These types of stents are commercially available from Boston Scientific Inc. located in Natick, Mass. under the tradename of Ultraflex®.

Figure 8:
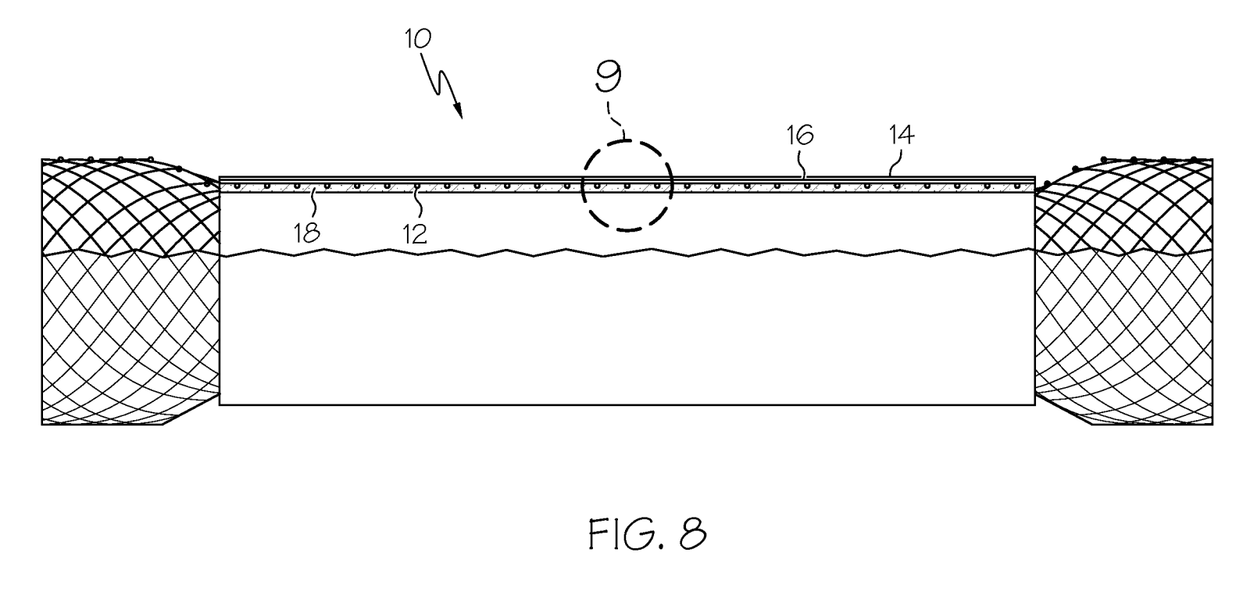
FIG. 8 is a side view of an embodiment of a stent according to the invention.

FIG. 8 is another embodiment of a stent 10 on which the dissolvable adhesive coating may be employed. In this embodiment, stent 10 is a self-expanding stent formed of a shape memory metal such as Nitinol® having a silicone covering. The stent has a braided wire construction. In this embodiment, stent 10 is shown having a silicone covering 18. Stent 10 is disposed on silicone covering 18 and is partially embedded therein.

Stent 10 may be fully, substantially or partially covered or lined with a polymeric covering 18. The covering may be in the form of a tubular structure. Nonlimiting examples of useful polymeric materials include polyesters, polypropylenes, polyethylenes, polyurethanes, polynaphthalenes, polytetrafluoroethylenes, expanded polytetrafluoroethylene, silicone, copolymers thereof and mixtures or combinations thereof. Desirably, the polymeric covering 18 is silicone. Stents of this type are described in commonly assigned US Patent Publication Nos. 2006/0276887 and 2008/0009934, each of which is incorporated by reference herein in its entirety. The covering can also be disposed on the external surfaces of the stent 10, or disposed on both the internal and external surfaces of the stent 10.

In this embodiment, stent 10 additionally has a coating of silicone or urethane 16 on the outer surface of the stent 10 and the dissolvable or degradable adhesive polymer layer 14.

In the event that the stent 10 does comprise a silicone or urethane coating 16, it is advantageous to roughen the surface in order to provide better adhesive bonding to the urethane or silicone surface.

Figure 9:
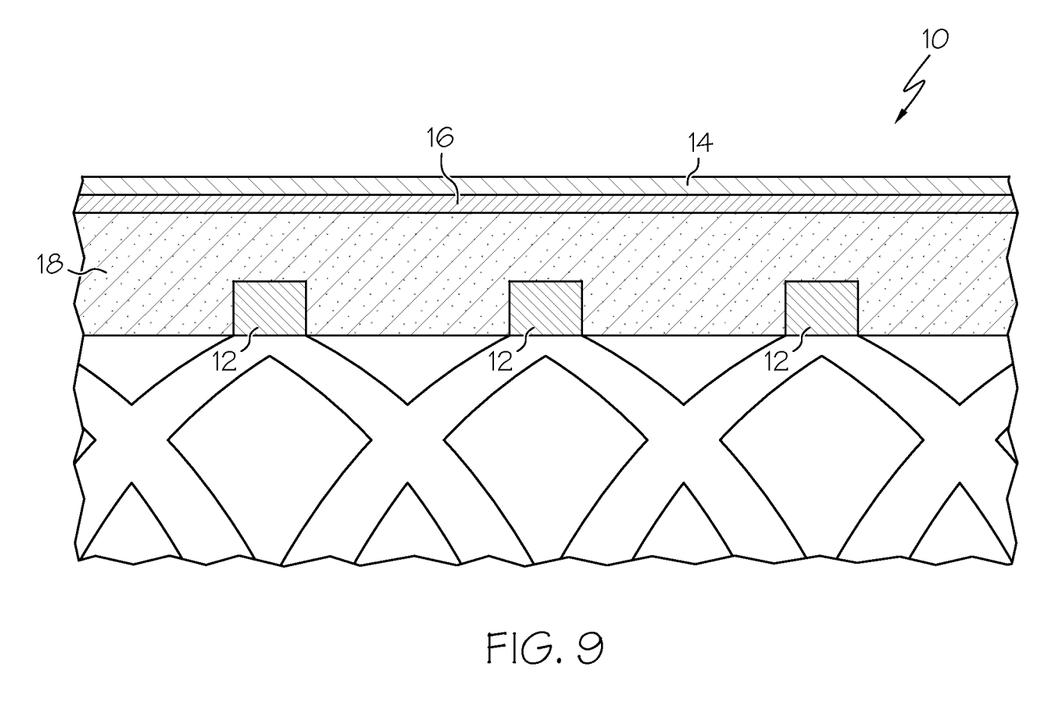
FIG. 9 is a cross-sectional view taken at section 9 in FIG. 8.

FIG. 9 is an enlarged view taken at section 9 in FIG. 8.

The adhesive 14 can be chemically bonded to, i.e. reacted with, the silicone or urethane covering 18, or crosslinked therewith. In one embodiment, the dissolvable or degradable adhesive polymer 14 is chemically bonded to a block of the covering polymer 18 in order to provide better adhesion between the stent covering 18 and the adhesive polymer 14.

In one embodiment, the silicone or urethane is activated, for example by plasma etching with oxygen plasma, to provide sites for chemical reaction with the adhesive.

The dissolvable or degradable adhesive polymer improves the adhesion of the stent to the body lumen within which the stent is disposed for treatment.

Suitably, the dissolvable or degradable adhesive polymer exhibits strong hydrogen bonding.

Polymers carrying a strong anionic charge have been found to provide better penetration with the mucosal tissue surface when the appropriate chain lengths are selected and create chain entanglement with the mucus network. Chain lengths may be anywhere from about 100 monomer units up to about 10,000 monomer units. Molecular weight may range from about 20,000 grams/mole up to a million or more, and suitably is greater than 50,000 grams/mole.

Polymer formulations having surface tension characteristics similar to those of the mucosal tissue will promote better wetting and improved intimate contact with the mucosal surface.

Examples of suitable dissolvable adhesive polymers include, but are not limited to, cellulose derivatives, hydrocolloids, acrylate copolymers, gums, polysaccharides, etc. Suitably, the surface tack of the adhesive is about 1 psi to about 15 psi and more suitably about 2 psi to about 14 psi. Examples of suitable cellulose derivatives include, but are not limited to, cellulose acetates, cellulose ethers and cellulose esters.

The rate of dissolution can be controlled by a number of factors including, the molecular weight of the polymer, or by the ratio of high molecular weight to low molecular weight polymer if a blend is employed, or the degree of substitution of ionic sites in the case of ionomers. The thickness, dissolution rate, surface characteristics (texture) and mechanical properties such as film strength can all be controlled and are significantly affected by the molecular weight of the polymer(s). Longer disintegration time and increased mechanical strength are expected for polymers having higher molecular weights.

In some embodiments, the dissolvable or degradable adhesive polymer will be coated on the external side of the stent and adhere to the body lumen epithelium, typically that of the airway, esophagus, bile duct, small intestine or colon.

In an alternative embodiment, the dissolvable or degradable adhesive polymer is delivered to the lumen before the stent is implanted. The adhesive can be delivered using a patch, a balloon, or a syringe, for example.

Suitably, the adhesive is activated with the contact of water, which allows delivery of the stent through a patient's body lumen using conventional means.

In one embodiment, the adhesive is applied to the lumen wall, e.g., the esophagus, for example, as a powder, by blowing the powder onto the esophageal wall via an air jet. The adhesive is hydrated and activates prior to placement of the stent. For example, the dissolvable adhesive can include a catalyst which when exposed to water dissolves and reacts with liberation of the catalyst, or the dissolvable adhesive polymer can include reactive groups that react in the presence of water.

In another embodiment, the adhesive is a two part adhesive wherein the first part is disposed on the outer surface of the stent and the second part is delivered to the body lumen such as via spraying on the lumen wall. The adhesive is activated when the first part and second part contact one another. If the first part and the second part are water soluble, the reaction rate is increased in the body. Furthermore, using a two part adhesive can allow for increased molecular weight in the reacted polymer which can enhance surface tack. For example, a dual lumen catheter may be employed wherein the distal end of the catheter includes a spray nozzle and one lumen provides air for spraying and the other lumen provides the adhesive fluid.

The adhesive can alternatively be coated with a water soluble polymer to facilitate delivery through a patient's body lumen. Suitable water soluble polymers include, but are not limited to, polyvinyl alcohol, polyethylene oxide, polyethylene glycol, high molecular weight carbohydrates and starches, etc.

Figure 10:
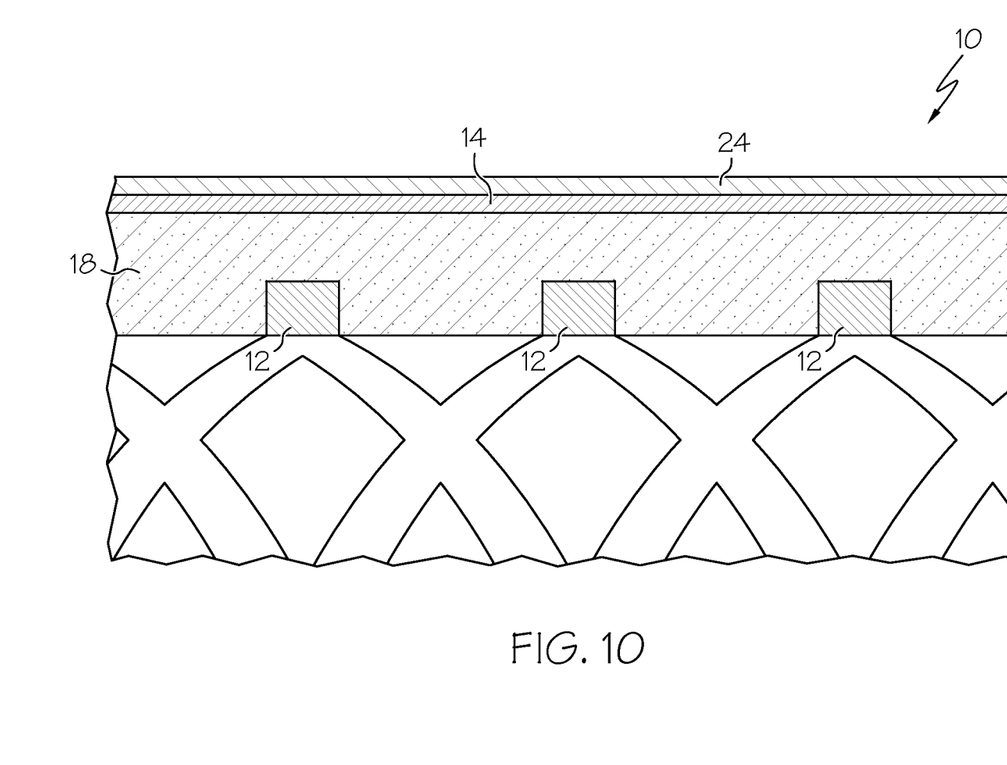
FIG. 10 is a partial cross-sectional view of a stent having a dissolvable adhesive polymer layer and a water soluble polymer layer disposed thereon.

FIG. 10 is a partial view of a stent 10 illustrating a water soluble polymer layer 24 disposed over the dissolvable or degradable adhesive layer 14. In this embodiment, stent 10 is shown having a covering layer 18. However, stent 10 could be a bare stent as well. Additionally, stent 10 could include silicone or urethane coating 16 as shown in FIGS. 8 and 9.

To provide additional contact with the lumen wall, additional exposed wires such as wire loops protruding from the surface could be coated with adhesive. The wires press into the soft tissue providing additional contact of the adhesive to the lumen wall.

Figure 11:
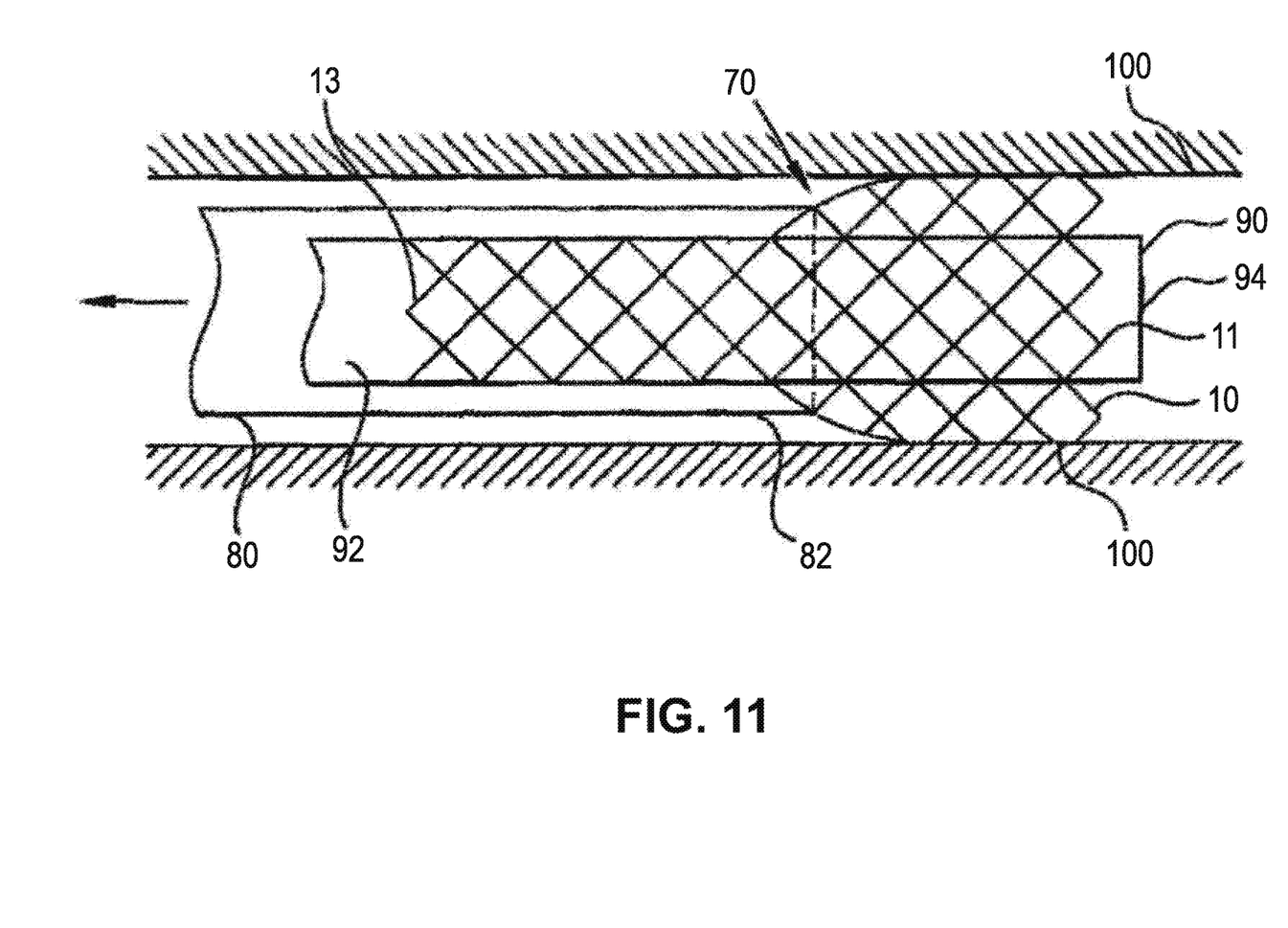
FIG. 11 is a planar depiction of partial deployment of a stent within a body lumen according to one embodiment of the invention.

FIG. 11 depicts partial deployment of the stent 10 with the device 70 of one embodiment of the invention. After the device 70 is placed within a body lumen 100, the exterior tube 80 may be retracted or slid away from the interior tube 90. As exterior tube 80 retracts proximally, the exposed distal portion 11 of the stent 10 expands against the walls of the body lumen 100. When distal end 82 of exterior tube 80 is retracted past the proximal end 13 of the stent 10 to the proximal portion 92 of the interior tube 90, the stent 10 may be fully deployed with the body lumen 100. The device 70 may be retracted from the body lumen 100, leaving the deployed stent 10 within the body lumen 100.

The description provided herein is not to be limited in scope by the specific embodiments described which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

The invention claimed is:

1. A self-expanding stent, the self-expanding stent having an inner surface and an outer surface, an entirety of the outer surface of the self-expanding stent comprising:
   a coating of silicone or urethane on the outer surface of the self-expanding stent, said coating of silicone or urethane comprising a roughened surface along an outer surface of the coating of silicone or urethane;
   a dissolvable adhesive polymer layer or degradable adhesive polymer layer covering the entire outer surface of the self-expanding stent over the coating of silicone or urethane, wherein the roughened surface facilitates adhesive bonding of the dissolvable adhesive polymer layer or degradable adhesive polymer layer to the outer surface of the coating of silicone or urethane, adhesive properties of the dissolvable adhesive polymer layer or degradable adhesive polymer layer are activated by exposure to an aqueous environment to increase adhesiveness of the dissolvable adhesive polymer layer or degradable adhesive polymer layer, the dissolvable adhesive polymer layer dissolves over time in the aqueous environment or the degradable adhesive polymer layer degrades over time in the aqueous environment, activation of the dissolvable adhesive polymer layer or the degradable adhesive polymer layer increases adhesion of the self-expanding stent to a body lumen and contributes an initial surface tack to the self-expanding stent that is resistant to migration of the self-expanding stent within the body lumen, wherein the dissolvable adhesive polymer layer or degradable adhesive polymer layer is configured to be in contact with an inner surface of the body lumen when the self-expanding stent is disposed within the body lumen; and
   a water soluble polymer coated on the dissolvable adhesive polymer layer or the degradable adhesive polymer layer.

2. The self-expanding stent of claim 1 wherein the initial surface tack of the dissolvable or degradable adhesive polymer layer is 2 psi to 14 psi.

3. The self-expanding stent of claim 1 wherein a surface tack of the dissolvable or degradable adhesive polymer layer decreases from the initial surface tack of the dissolvable or degradable adhesive polymer layer over time as the polymer dissolves or degrades.

4. The self-expanding stent of claim 1 wherein the dissolvable or degradable adhesive polymer layer dissolves or degrades in 4 weeks to 6 weeks after implantation in the body lumen.

5. The self-expanding stent of claim 1 wherein said dissolvable adhesive polymer layer or said degradable adhesive polymer layer is configured to have adhesion to human tissue.

6. The self-expanding stent of claim 1 wherein said dissolvable adhesive polymer layer exhibits strong hydrogen bonding.

7. The self-expanding stent of claim 1 wherein said dissolvable adhesive polymer layer or said degradable adhesive polymer layer comprises chain lengths which are configured to provide chain entanglement with a mucous network.

8. The self-expanding stent of claim 1 wherein said dissolvable adhesive polymer layer comprises at least one member selected from the group consisting of cellulose derivatives, hydrocolloids, acrylate copolymers, gums and polysaccharides.

9. The self-expanding stent of claim 1 wherein said water soluble polymer comprises at least one member selected from the group consisting of polyacrylic acid, polyvinyl alcohol, polyvinyl pyrrolidone, polyethylene oxide, polypropylene oxide, polyethylene glycol, high molecular weight carbohydrates, starches, and block or random copolymers thereof.

10. The self-expanding stent of claim 1 further comprising a covering disposed on at least a portion of the inner surface of the self-expanding stent.

11. The self-expanding stent of claim 1 wherein said coating of silicone or urethane is chemically bonded or crosslinked with said dissolvable adhesive polymer layer or with said degradable adhesive polymer layer.

12. The self-expanding stent comprising:
   a self-expanding stent body having an inner surface and an outer surface;
   a covering of silicone or urethane disposed on an entirety of the outer surface of the self-expanding stent body such that the covering of silicone or urethane directly contacts the outer surface of the self-expanding stent body, wherein said covering of silicone or urethane comprises a roughened outer surface along an entirety of the covering of silicone or urethane to facilitate adhesive bonding to the roughened outer surface of the covering of silicone or urethane;

a dissolvable adhesive polymer layer or degradable adhesive polymer layer covering an entirety of the roughened outer surface of the covering of silicone or urethane such that the dissolvable adhesive polymer layer or degradable adhesive polymer layer directly contacts the roughened outer surface of the covering of silicone or urethane, wherein adhesive properties of the dissolvable adhesive polymer layer or degradable adhesive polymer layer are activated by exposure to an aqueous environment to increase adhesiveness of the dissolvable adhesive polymer layer or degradable adhesive polymer layer, wherein the dissolvable adhesive polymer layer or the degradable adhesive polymer layer degrades over time in the aqueous environment, wherein activation of the dissolvable adhesive polymer layer or the degradable adhesive polymer layer increases adhesion of the self-expanding stent to a body lumen and contributes an initial surface tack to the self-expanding stent that is resistant to migration of the self-expanding stent within the body lumen, wherein the dissolvable adhesive polymer layer or degradable adhesive polymer layer is configured to be in contact with an inner surface of the body lumen when the self-expanding stent is disposed within the body lumen;

a water soluble polymer coated on the dissolvable adhesive polymer layer or the degradable adhesive polymer layer such that the water soluble polymer directly contacts the dissolvable adhesive polymer layer or the degradable adhesive polymer layer.

13. The self-expanding stent of claim 12, wherein said covering of silicone or urethane is chemically bonded or crosslinked with said dissolvable adhesive polymer layer or with said degradable adhesive polymer layer.

14. The self-expanding stent of claim 12, wherein said dissolvable adhesive polymer layer or said degradable adhesive polymer layer comprises chain lengths which are configured to provide chain entanglement with a mucous network.

15. A self-expanding stent having an inner surface and an outer surface, an entirety of the outer surface of the self-expanding stent comprising:

a coating of silicone or urethane on the outer surface of the self-expanding stent, said coating of silicone or urethane comprising a roughened surface along an entirety of an outer surface of the coating of silicone or urethane;

a dissolvable adhesive polymer layer or degradable adhesive polymer layer covering the entire outer surface of the self-expanding stent over the coating of silicone or urethane, wherein the roughened surface facilitates adhesive bonding of the dissolvable adhesive polymer layer or degradable adhesive polymer layer to the outer surface of the coating of silicone or urethane, adhesive properties of the dissolvable adhesive polymer layer or degradable adhesive polymer layer are activated by exposure to an aqueous environment to increase adhesiveness of the dissolvable adhesive polymer layer or degradable adhesive polymer layer, the dissolvable adhesive polymer layer dissolves over time in the aqueous environment or the degradable adhesive polymer layer degrades over time in the aqueous environment, activation of the dissolvable adhesive polymer layer or the degradable adhesive polymer layer increases adhesion of the self-expanding stent to a body lumen and contributes an initial surface tack to the self-expanding stent that is resistant to migration of the self-expanding stent within the body lumen, wherein the dissolvable adhesive polymer layer or degradable adhesive polymer layer is configured to be in contact with an inner surface of the body lumen when the self-expanding stent is disposed within the body lumen; and a water soluble polymer coated on the dissolvable adhesive polymer layer or the degradable adhesive polymer layer;

wherein the self-expanding stent is configured to be delivered with an interior tube extending through the self-expanding stent and an exterior tube surrounding the self-expanding stent and maintaining the stent in a first compact configuration, wherein the self-expanding stent is configured such that when the exterior tube is slideably retracted from the self-expanding stent, the self-expanding stent fully deploys to a second expanded configuration.

16. The self-expanding stent of claim 1, further comprising wire loops protruding from the outer surface of the elf-expanding stent, the wire loops coated with the dissolvable or degradable adhesive polymer layer.

17. The self-expanding stent of claim 12, further comprising wire loops protruding from the outer surface of the elf-expanding stent body, the wire loops coated with the dissolvable or degradable adhesive polymer layer.

18. The self-expanding stent of claim 15, further comprising wire loops protruding from the outer surface of the elf-expanding stent, the wire loops coated with the dissolvable or degradable adhesive polymer layer.

* * * * *